US006670492B2

(12) United States Patent
Hofen et al.

(10) Patent No.: US 6,670,492 B2
(45) Date of Patent: Dec. 30, 2003

(54) PROCESS FOR THE EXPOXIDATION OF OLEFINS

(75) Inventors: Willi Hofen, Rodenbach (DE); Georg Thiele, Hanau (DE)

(73) Assignees: Degussa AG, Düsseldorf (DE); UHDE GmbH, Dortmund (DE)

(*) Notice: Subject to any disclaimer, the term of this patent is extended or adjusted under 35 U.S.C. 154(b) by 0 days.

(21) Appl. No.: 10/203,186

(22) PCT Filed: Feb. 3, 2001

(86) PCT No.: PCT/EP01/01167
§ 371 (c)(1),
(2), (4) Date: Oct. 4, 2002

(87) PCT Pub. No.: WO01/57011
PCT Pub. Date: Aug. 9, 2001

(65) Prior Publication Data
US 2003/0092920 A1 May 15, 2003

(30) Foreign Application Priority Data
Feb. 7, 2000 (EP) .............................. 00102543

(51) Int. Cl.$^7$ .............................. C07D 301/12
(52) U.S. Cl. ....................... 549/531; 549/523
(58) Field of Search .................... 49/531, 523

(56) References Cited

U.S. PATENT DOCUMENTS

| | | |
|---|---|---|
| 2,870,171 A | 1/1959 | Gable |
| 4,410,501 A | 10/1983 | Taramasso et al. |
| 4,833,260 A | 5/1989 | Neri et al. |
| 5,523,426 A | 6/1996 | Jubin, Jr. et al. |
| 5,591,875 A | 1/1997 | Chang et al. |
| 5,599,955 A | 2/1997 | Vora et al. |
| 5,620,935 A | 4/1997 | Thiele |
| 5,675,026 A | 10/1997 | Thiele |
| 5,760,253 A | 6/1998 | Danner et al. |
| 5,849,937 A | 12/1998 | Jubin, Jr. et al. |
| 5,849,938 A | 12/1998 | Reuter et al. |
| 5,912,367 A | 6/1999 | Chang |
| 6,042,807 A | 3/2000 | Faraj |
| 6,063,941 A | 5/2000 | Gilbeau |
| 6,372,924 B2 | 4/2002 | Thiele |

FOREIGN PATENT DOCUMENTS

| | | |
|---|---|---|
| DE | 196 23 611 | 12/1997 |
| DE | 197 23 950 | 12/1998 |
| DE | 197 54 185 | 2/1999 |
| DE | 198 35 907 | 2/2000 |
| EP | 0 100 118 | 2/1984 |
| EP | 0 100 119 | 2/1984 |
| EP | 0 106 671 | 4/1984 |
| EP | 0 230 349 | 7/1987 |
| EP | 0 230 949 | 8/1987 |
| EP | 0 568 336 | 11/1993 |
| EP | 0 568 337 | 11/1993 |
| EP | 0 583 828 | 2/1994 |
| EP | 0 645 473 | 3/1995 |
| EP | 0 659 473 | 6/1995 |
| EP | 0 712 852 | 5/1996 |
| EP | 0 719 768 | 7/1996 |
| EP | 0 757 045 | 2/1997 |
| EP | 0 795 537 | 9/1997 |
| EP | 0 827 765 | 3/1998 |
| EP | 0 930 308 | 7/1999 |
| EP | 0 936 219 | 8/1999 |
| EP | 1 066 711 | 12/1999 |
| EP | 1 122 248 | 8/2001 |
| EP | 1 138 387 | 10/2001 |
| EP | 1 221 442 | 7/2002 |
| JP | 2166636 | 6/1990 |
| WO | WO 97/47613 | 12/1997 |
| WO | WO 97/47614 | 12/1997 |
| WO | WO 99/01445 | 1/1999 |
| WO | WO 99/07690 | 2/1999 |
| WO | WO 99/11639 | 3/1999 |
| WO | WO 00/07695 | 2/2000 |
| WO | WO 00/17178 | 3/2000 |

*Primary Examiner*—Ba K. Trinh
(74) *Attorney, Agent, or Firm*—Smith, Gambrell & Russell

(57) ABSTRACT

The invention described herein relates to a process for the catalytic epoxidation of olefins with hydrogen peroxide in a continuous flow reaction system, wherein a gaseous phase containing an olefin and a liquid phase containing the hydrogen peroxide is present in the reaction system and the gaseous phase flows in countercurrent to the liquid phase.

9 Claims, 2 Drawing Sheets

PROCESS FOR THE EXPOXIDATION OF OLEFINS

This application is a 371 of PCT/EP01/01167, filed Feb. 3, 2001.

PRIOR ART

From EP-A 100 119 it is known that propene can be converted by hydrogen peroxide into propene oxide if a titanium-containing zeolite is used as catalyst.

Unreacted hydrogen peroxide cannot be recovered economically from the epoxidation reaction mixture. Furthermore, unreacted hydrogen peroxide involves additional effort and expenditure in the working up of the reaction mixture. The epoxidation of propene is therefore preferably carried out with an excess of propene and up to a high hydrogen peroxide conversion. In order to achieve a high hydrogen peroxide conversion it is advantageous to use a continuous flow reaction system. Such a reaction system may comprise either one or more tubular flow reactors or an arrangement of two or more flow mixing reactors connected in series. Examples of flow mixing reactors are stirred tank reactors, recycle reactors, fluidised bed reactors and fixed bed reactors with recycling of the liquid phase.

In order to achieve a high reaction velocity as high a propene concentration as possible in the liquid phase is necessary. The reaction is therefore preferably carried out under a propene atmosphere at elevated pressure.

The decomposition of hydrogen peroxide with the formation of molecular oxygen always occurs to a slight extent as a secondary reaction on the titanium silicalite catalyst. In order to be able to operate the epoxidation process reliably on an industrial scale the oxygen that is formed must be removed from the reaction system. This is effected most simply by flushing the oxygen out with a propene waste gas stream.

EP-A 659 473 describes an epoxidation process that combines these features. In this connection a liquid mixture of hydrogen peroxide, solvent and propene is led over a succession of fixed bed reaction zones connected in series, wherein the liquid phase is removed from each reaction zone, is led over an external heat exchanger to extract the heat of reaction, and the major proportion of this liquid phase is then recycled to this reaction zone and a minor proportion of the liquid phase is passed to the next zone. The individual reaction zones behave as flow mixing reactors on account of the liquid recycling over the fixed bed. At the same time gaseous propene is fed in together with the liquid feed stock mixture, is guided in a parallel stream to the liquid phase over the fixed bed reaction zones, and is extracted at the end of the reaction system in addition to the liquid reaction mixture as an oxygen-containing waste gas stream. Although this reaction procedure enables the propene oxide yield to be raised compared to conventional tubular reactors without the temperature control described in EP-A 659 473, it nevertheless involves considerable additional costs on account of the complexity of the reaction system required to carry out the process. Furthermore, the described raised yield can only be realised if the propene oxide contained in the waste gas stream is recovered. This necessitates an additional process stage, which in turn adds further to the costs of the process.

The object of the present invention is accordingly to provide a simple inexpensive process for the epoxidation of olefins with hydrogen peroxide, with which high conversions can be achieved combined with a high product yield and which can be carried out using conventional reaction systems.

SUBJECT OF THE INVENTION

This object is achieved by a process for the catalytic epoxidation of olefins with hydrogen peroxide in a continuous flow reaction system wherein a gaseous phase containing an olefin and a liquid phase containing the hydrogen peroxide are present in the reaction system and the gaseous phase is fed in countercurrent to the liquid phase.

An important advantage of the countercurrent arrangement according to the invention is the reduction in the amount of propene oxide that is discharged from the reaction system together with the oxygen-containing propene waste gas stream, and the resultant decreased expenditure on recovering propene oxide from this waste gas stream. As small a loss of propene oxide as possible is desired in order to achieve a high product yield according to the invention.

The countercurrent arrangement according to the invention of gaseous olefin and liquid reaction mixture in the reaction system may be accomplished in various ways depending on the chosen reaction system. In this connection reaction systems are suitable in which there is no complete back-mixing relative to the overall system, i.e. reaction systems whose residence time spectrum exhibits a maximum, or reaction systems involving plug flow.

If the epoxidation of olefins is carried out in a tubular flow reactor, then the gas stream containing the olefin is guided in countercurrent to the liquid phase within the reactor. In this connection the liquid stream is preferably led from the top downwards through the reactor, while the olefin flows from the bottom upwards through the reactor in the form of a gas stream. The reactor may be operated as a bubble column with a continuous liquid phase, as well as a trickle reactor with a continuous gas phase. The catalyst may be employed either as a suspension in the liquid phase or in the form of a fixed bed, wherein the fixed bed may be designed both as a random catalyst packing as well as an ordered packing of coating monoliths or distribution bodies. Preferably a tubular flow reactor is used as a fixed bed reactor with a random catalyst packing and continuous liquid phase.

In order to be able to operate the process continuously when changing and/or regenerating the epoxidation catalyst, two or more tubular flow reactors may if desired also be operated in parallel or in series in the aforedescribed manner.

If the epoxidation of olefins is carried out in a succession of two or more tubular flow reactors connected in series, the substance streams of liquid phase and gaseous phase within a flow reactor may be guided either in co-current or in countercurrent, the substance streams being guided in countercurrent between the tubular flow reactors.

In an alternative embodiment the reaction system may comprise several reactors connected in series that are chosen independently of one another from flow mixing reactors and tubular flow reactors, the substance streams of liquid phase and gaseous phase being guided in countercurrent between the reactors. For example, flow mixing reactors and tubular flow reactors may also be used in combination within the reaction system consisting of reactors connected in series. Preferably, in this connection one or more flow mixing reactors are connected in series with a final tubular flow reactor. The particular advantage of such a reaction system is that the heat of reaction can be particularly easily extracted from the flow mixing reactors in which the major proportion of the reaction turnover takes place. The use of a final tubular flow reactor ensures that the hydrogen peroxide conversion takes place as fully as possible. Stirred tank reactors, recycle reactors, jet reactors with liquid circulation, or fixed bed reactors with a liquid circulation over the fixed bed are for example suitable as flow mixing reactors.

Using the process according to the invention olefins can be epoxidised that are at least partially in the gaseous phase under the chosen reaction conditions. This applies in particular to olefins with 2 to 6 carbon atoms. The process according to the invention is most particularly suitable for the epoxidation of propene to propene oxide.

For economic reasons it would be preferred for an industrial scale process to use propene not in a pure form but as a technical mixture with propane that as a rule contains 1 to 15 vol. % of propane. Since propene is consumed in the epoxidation reaction, propane accumulates in the gas stream during its passage through the reaction system, which in the case of a co-current flow arrangement leads to a decrease in the reaction velocity and to differences in the generation of heat through the exothermal epoxidation reaction along the chain of reactors. These disadvantages can be avoided by the countercurrent flow of gas phase and liquid phase according to the invention. Furthermore the propene oxide yield is raised even in the presence of propane in the feed stream compared to a co-current feed with the countercurrent feed of the substance streams. From this it is clear that, by means of the process according to the invention, not only can a high turnover and a high propene oxide yield be achieved with low expenditure on apparatus, but also the use of technical propene with up to 15% of propane does not have a deleterious effect on the reaction and the product yield. The economy of the process according to the invention is further improved on account of the usability of relatively cheap starting materials.

Crystalline, titanium-containing zeolites of the composition $(TiO_2)_x(SiO_2)_{1-x}$ where x is from 0.001 to 0.05 and having a MFI or MEL crystalline structure, known as titanium silicalite-1 and titanium silicalite-2, are suitable as catalysts for the epoxidation process according to the invention. Such catalysts may be produced for example according to the process described in U.S. Pat. No. 4,410,501. The titanium silicalite catalyst may be employed as a powder or as a shaped catalyst in the form of granules, extrudates or shaped bodies. For the forming process the catalyst may contain 1 to 99% of a binder or carrier material, all binders and carrier materials being suitable that do not react with hydrogen peroxide or with the epoxide under the reaction conditions employed for the epoxidation. Granules corresponding to EP-A 893 158 are preferably used as suspension catalysts. Extrudates with a diameter of 1 to 5 mm are preferably used as fixed bed catalysts.

The hydrogen peroxide is used in the process according to the invention in the form of an aqueous solution with a hydrogen peroxide content of 1 to 90 wt. %, preferably 10 to 70 wt. % and particularly preferably 30 to 50 wt. %. The hydrogen peroxide may be used in the form of the commercially available, stabilised solutions. Also suitable are unstabilised, aqueous hydrogen peroxide solutions such as are obtained in the anthraquinone process for producing hydrogen peroxide.

The reaction is preferably carried out in the presence of a solvent in order to increase the solubility of the olefin, preferably propene, in the liquid phase. Suitable as solvent are all solvents that are not oxidised or are oxidised only to a slight extent by hydrogen peroxide under the chosen reaction conditions, and that dissolve in an amount of more than 10 wt. % in water. Preferred are solvents that are completely miscible with water. Suitable solvents include alcohols such as methanol, ethanol or tert.-butanol; glycols such as for example ethylene glycol, 1.2-propanediol or 1,3-propanediol; cyclic ethers such as for example tetrahydrofuran, dioxane or propylene oxide; glycol ethers such as for example ethylene glycol monomethyl ether, ethylene glycol monoethyl ether, ethylene glycol monobutyl ether or propylene glycol monomethyl ether, and ketones such as for example acetone or 2-butanone. Methanol is particularly preferably used as solvent.

The process according to the invention for the epoxidation of olefins, preferably propene, is carried out at a temperature of −10° to 100° C., preferably at 20° to 70° C. The olefin is preferably employed in excess relative to the hydrogen peroxide in order to achieve a significant consumption of hydrogen peroxide, the molar ratio of olefin, preferably propene, to hydrogen peroxide preferably being chosen in the range from 1.1 to 10. When adding a solvent the amount of solvent is preferably chosen so that only a liquid phase is present in the reaction mixture. The solvent is preferably added in a weight ratio of 0.5 to 20 relative to the amount of hydrogen peroxide solution used. The amount of catalyst employed may be varied within wide limits and is preferably chosen so that a hydrogen peroxide consumption of more than 90%, preferably more than 95%, is achieved within 1 minute to 5 hours under the employed reaction conditions.

In a preferred embodiment of the process according to the invention propene is used that may contain between 0% and 15% of propane. Propene may be fed as a liquid as well as in gaseous form into the reaction system. The amount of propene that is fed in is chosen so that under the reaction conditions in the reactors a gas phase is formed consisting predominantly of propene, and so that from the first reactor of the reaction system a waste gas can be removed whose oxygen content lies outside the explosion limits for propylene-oxygen mixtures. The pressure in the reaction system is preferably chosen to be between 50% and 100% of the saturated vapour pressure of propylene at the reaction temperature.

The present invention will be illustrated hereinafter with the aid of figures and examples for the epoxidation of propene.

FIG. 1 shows a tubular flow reactor. Stream 1 denotes the feed stream of the liquid reaction phase, stream 2 denotes the outlet stream of the liquid reaction phase, stream 3 denotes the feed stream of the gaseous component, and stream 4 denotes the waste gas stream. These designations are also retained for the other figures.

FIG. 2 illustrates the flow of the substance streams for three reactors connected in series. The liquid feedstocks are fed with stream 1 into the first reactor. From the first reactor the liquid reaction mixture is led via the streams 5 and 6 into the second and third reactors and is removed in liquid form as stream 2 from the third reactor. Propene, optionally mixed with propane, is fed with the stream 3 into the third reactor and together with the streams 7 and 8 is led in gaseous form via the second reactor into the first reactor. From the first reactor a waste gas stream is removed via the stream 4, the waste gas stream containing, in addition to unreacted propene and possibly propane, the molecular oxygen formed by decomposition of hydrogen peroxide during the epoxidation reaction.

FIG. 3 shows by way of example a system consisting of three stirred tank reactors connected in series for the epoxidation using a suspension catalyst, wherein the system is operated according to the invention with countercurrent flow of liquid phase and propene gas, and the numbering of the substance streams agrees with FIG. 2.

When tubular flow reactors are connected in series, the flow of the substance streams within a reactor may take place both in countercurrent and in co-current.

EXAMPLE

Figure 1:
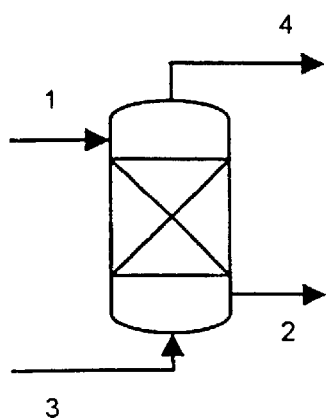
Figure 2:
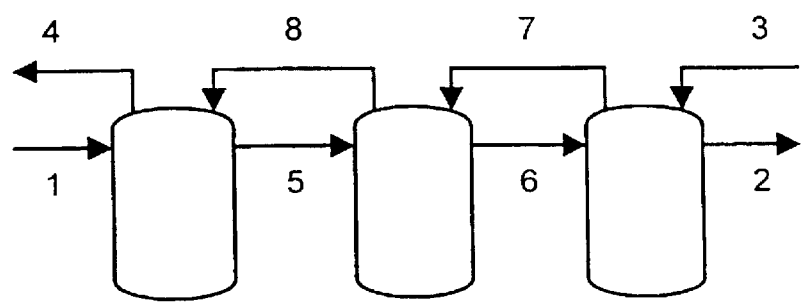
Figure 3:
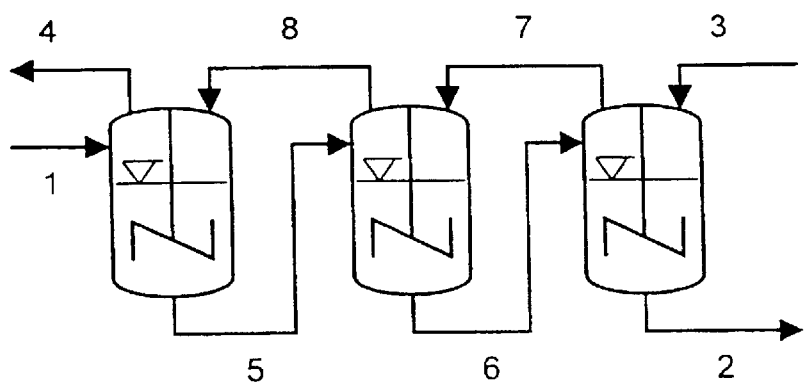
Figure 4:
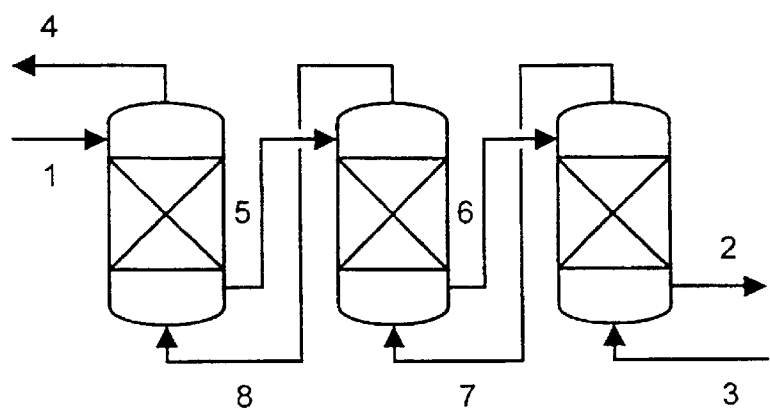
FIG. 4 shows by way of example a system consisting of three fixed bed reactors connected in series with countercurrent flow within the reactors, wherein the substance streams of liquid phase and propene gas flow in countercurrent between the reactors in the manner according to the invention.
Figure 5:
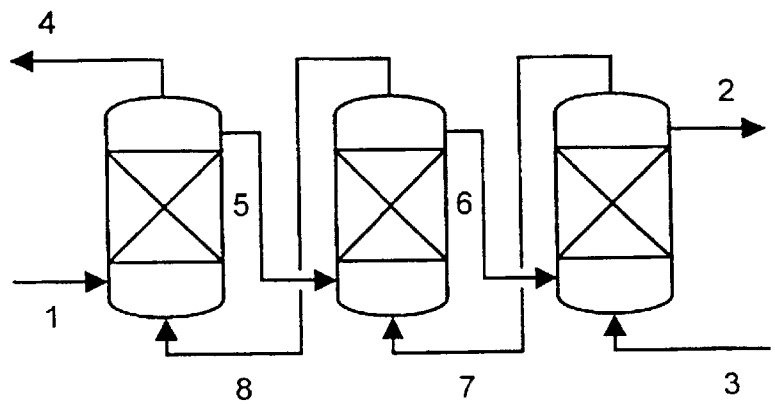
FIG. 5 shows by way of example a system consisting of three fixed bed reactors connected in series with co-current flow within the reactors, wherein the substance streams of liquid phase and propene gas flow in countercurrent between the reactors in the manner according to the invention. In both diagrams the numbering of the individual substance streams agrees with FIG. 2.
Figure 6:
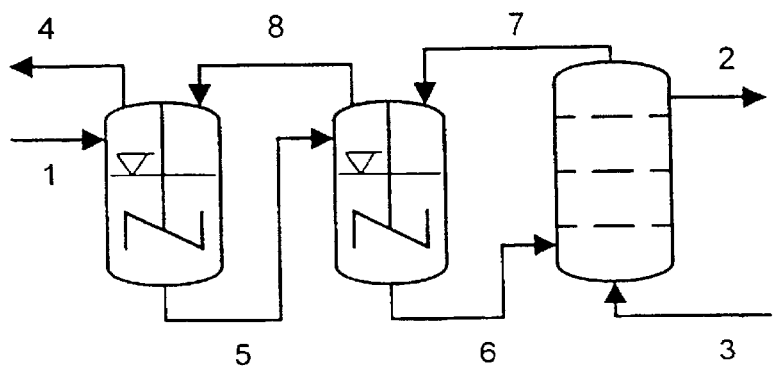
FIG. 6 shows by way of example the combination of two stirred tank reactors with a bubble column reactor operating in co-current flow for the epoxidation using a suspension catalyst, the substance streams of liquid phase and propylene gas flowing in countercurrent between the reactors in the manner according to the invention. The numbering of the individual substance streams agrees with FIG. 2.

In an arrangement consisting of two stirred tank reactors and a tubular flow reactor with an overall volume of 6.25 liters, which are connected to one another corresponding to FIG. 6, 43 wt. % aqueous hydrogen peroxide solution is fed into the first reactor at a rate of 1045 g/h in parallel with a 2.0 wt. % suspension of titanium silicalite in methanol at a rate of 2630 g/h (stream 1). 1120 g/h of propene in gaseous form are fed at the same time from below into the third reactor (stream 3). The three reactors are thermostatically controlled at a temperature of 65° C. and the pressure in all three reactors is maintained at an excess pressure of 15.0 bar by means of a pressure retention valve on the first reactor. 215 g/h of unreacted propene with an oxygen content of 0.6 vol. % are removed at the pressure retention valve (stream 4). The hydrogen peroxide concentration is determined by redox titration and the contents of propene oxide, 1-methoxy-2-propanol, 2-methoxy-1-propanol and 12-propanediol are determined by gas chromatography at regular intervals in the liquid reaction mixture (stream 2) removed from the third reactor. When the stationary operational state has been reached the hydrogen peroxide conversion is 96.8%, the propene oxide yield referred to converted hydrogen peroxide is 90.3%, and the propene oxide selectivity, calculated as the ratio of the concentration of propene oxide to the sum of the concentrations of the products propene oxide, 1-methoxypropanol, 2-methoxypropanol and 1,2-propanediol, is 94.5%.

What is claimed is:

1. Process for the catalytic epoxidation of olefins with hydrogen peroxide in a continuous flow reaction system, wherein a gaseous phase containing an olefin and a liquid phase containing the hydrogen peroxide is present in the reaction system, characterised in that the gaseous phase is guided in countercurrent to the liquid phase.

2. Process according to claim 1, characterised in that the reaction system is selected from one or more tubular flow reactors connected in series or in parallel.

3. Process according to claim 2, characterised in that the reaction system comprises several tubular flow reactors connected in series, the substance streams of liquid phase and gaseous phase flowing either in co-current or in countercurrent within a tubular flow reactor, and the substance streams flowing in countercurrent between the tubular flow reactors.

4. Process according to claim 1, characterised in that the reaction system comprises several reactors connected in series that are selected independently of one another from flow mixing reactors and tubular flow reactors, the substance streams of liquid phase and gaseous phase flowing in countercurrent between the reactors.

5. Process according to claim 1, characterised in that the catalyst is suspended in the liquid reaction phase.

6. Process according to claim 2, characterised in that the catalyst is used in the form of a fixed bed.

7. Process according to claim 1, characterised in that a titanium-containing zeolite is used as catalyst.

8. Process according to claim 1, characterised in that the olefin is propene.

9. Process according to claim 8, characterised in that a propene feed stream is used that in addition contains up to 15 vol. % of propane.

\* \* \* \* \*

UNITED STATES PATENT AND TRADEMARK OFFICE
CERTIFICATE OF CORRECTION

PATENT NO. : 6,670,492 B2
DATED : December 30, 2003
INVENTOR(S) : Hofen, Willi et al.

It is certified that error appears in the above-identified patent and that said Letters Patent is hereby corrected as shown below:

<u>Title page,</u>
Item [54], Title, should read as follows: -- PROCESS FOR THE EPOXIDATION OF OLEFINS --
Item [73], Assignees, should read as follows:
-- Degussa AG, Düsseldorf (DE);
   Uhde GmbH, Dortmund (DE) --

Signed and Sealed this

Sixth Day of July, 2004

JON W. DUDAS
*Acting Director of the United States Patent and Trademark Office*